United States Patent [19]
Dobson

US005695630A

[11] Patent Number: 5,695,630
[45] Date of Patent: Dec. 9, 1997

[54] METHOD AND APPARATUS FOR ADDING MERCURY IONS TO A FLUID SAMPLE

[75] Inventor: John V. Dobson, Hartlepool, Great Britain

[73] Assignee: The Secretary of State for Defence in Her Britannic Majesty's Government of the United Kingdom of Great Britain and Northern Ireland, Hants, United Kingdom

[21] Appl. No.: 617,839

[22] PCT Filed: Sep. 13, 1994

[86] PCT No.: PCT/GB94/01995

§ 371 Date: May 28, 1996

§ 102(e) Date: May 28, 1996

[87] PCT Pub. No.: WO95/08111

PCT Pub. Date: Mar. 23, 1995

[30] Foreign Application Priority Data

Sep. 14, 1993 [GB] United Kingdom ............... 9318958

[51] Int. Cl.[6] ............................ C25B 9/00; C25B 11/18
[52] U.S. Cl. ..................... 205/687; 204/250; 204/251; 204/275; 204/219
[58] Field of Search ............................ 204/219, 220, 204/250, 251, 275; 205/687

[56] References Cited

U.S. PATENT DOCUMENTS

| | | | |
|---|---|---|---|
| 2,289,611 | 7/1942 | Wallace | 204/250 X |
| 2,500,284 | 3/1950 | Heyrovsky | 204/219 X |
| 2,835,631 | 5/1958 | Metcalf et al. | 204/251 X |
| 3,808,116 | 4/1974 | Webb. | |
| 4,661,210 | 4/1987 | Tenygl. | |
| 4,917,781 | 4/1990 | Sharifian et al. | 204/251 X |

FOREIGN PATENT DOCUMENTS

| | | | |
|---|---|---|---|
| 0409705 | 1/1991 | European Pat. Off. | |
| 3404283 | 8/1985 | Germany. | |

*Primary Examiner*—Donald R. Valentine
*Attorney, Agent, or Firm*—Nixon & Vanderhye P.C.

[57] ABSTRACT

This invention relates to apparatus for adding mercury ions to a sample fluid within a flow-through sensor system comprising housing means in fluid connection with a main sample stream conduit via a semi-permeable part (2.11), a first electrode (2.8) located within the housing means preferably designed so that it would be in electrical contact with only the mercury when the mercury is located within the housing means, and a second electrode (2.12) located ideally within the main sample stream conduit, the apparatus being arranged such that when mercury is located within housing means and an electrical current is passed between the first and second electrodes, mercury ions are formed in the housing means which then are able to migrate from the housing means via the semi-permeable part into the main sample stream conduit. The housing means can comprise a container coated with or made from an inert shroud such as polytetrafluoroethylene, the inert shroud comprising a semi-permeable member, for example, a sintered end cap made from a hydrophobic, porous, close-pored durable plastic material.

8 Claims, 3 Drawing Sheets

METHOD AND APPARATUS FOR ADDING MERCURY IONS TO A FLUID SAMPLE

BACKGROUND OF THE INVENTION

1. Field of the Invention

The invention relates to a voltammetric method and apparatus for coating an electrode end thus providing, in one instance, a mercury electrode for use in a sensor system.

2. Discussion of Prior Art

There are various methods by which ions can be generated within a solution. One such method is the dissolution of either an anode or cathode which are located within the solution by passing a current between the anode and cathode. Patent EP-0 409,705 discloses apparatus where the dissolution of either the anode or cathode can be controlled so that the concentration of the ions generated are controlled by controlling the amount of current which passes between the anode or cathode. The anode and cathode are solid and are located directly within the solution.

Many analytical procedures involving the determination of substances, additives or contaminants within a sample solution employ the use of mercury film electrodes. Mercury film electrodes are used to determine pollutant species in the environment. It is therefore desirable to ensure that the provision of a mercury film electrode does not itself contribute to an increase of pollutants in the environment. Many methods which rely upon the use of mercury to produce a mercury film on an electrode for use in analytical procedure are fraught with contamination difficulties. The use of mercury poses a hazard, even though it is typically used at very low concentrations, in the order of $10^{-6}$ M to $10^{-4}$ M. Despite this relatively low concentration, its release into the environment is still undesirable. Therefore, the apparatus disclosed in Patent EP-O-P 409,705 would not be suitable in a situation where mercury ions are required. The mercury, which is a liquid, would be in direct contact with the solution and therefore would mix with the solution.

It follows that the control of, and where possible, the recovery of the hazardous chemical species is desirable.

Hitherto, mercury has been deposited within a fluid sample flow using standard dissolution techniques, such as dissolving mercury salt pellets in the fluid sample. Where appropriate, the mercury can be absorbed onto an electrode's surface from the fluid sample by the application of an electric potential. Since mercury salts are particularly soluble, retaining acceptable concentrations of mercury in solution over relatively long periods of time can be problematical.

It is therefore the object of the present invention to provide an apparatus and method which overcomes or at least mitigates the above disadvantages.

SUMMARY OF THE INVENTION

According to one aspect of the present invention there is provided an apparatus for adding mercury ions to a sample fluid within a flow-through sensor system comprising housing means, at least part of which is in fluid connection with a main sample stream conduit, at least part of the housing means in fluid connection with the main sample stream conduit being semi-permeable;

a first electrode located within the housing means which is designed so that it would be in direct electrical contact only with the mercury when the mercury is located within the housing means;

and a second electrode located either within the housing means or within the main sample stream conduit;

the apparatus being arranged such that when mercury is located within the housing means and an electrical current is passed between the first and second electrodes, mercury ions are formed in the housing means which then are then able to migrate from the housing means via the semi-permeable part into the main sample stream conduit.

It will be apparent to those skilled in the art that mercury metal dissolves under the influence of an electrical potential between two electrodes to form mercury ions. This phenomena is the basis on which the present invention operates.

One advantage of the present invention is that the quantity of mercury ions produced can be controlled, enabling pre-determined amounts to be introduced into a system. This is achieved by using pre-determined amounts of current, the amounts of current usually being very small. Further, the apparatus can operate for very long periods, many weeks, before requiring attention such as maintenance which would consist of simply adding mercury into the housing means. This is very favourable when compared to the use of mercury salts which require replacement at much more frequent intervals.

Preferably, the second electrode is located within the main stream conduit, ideally, in close proximity to the semi-permeable part of the housing means.

Analysis electrodes can be located within the main stream sample conduit down stream from the housing means and electrodes. The mercury ions would be attracted to the analysis electrode when a potential is applied, mercury being deposited onto the analysis electrode.

Another electrochemical system for trapping the mercury species can be positioned down stream of the analysis electrode. This system would trap the species is liberated from the analysis electrode. This process enables the chemical species to be removed from the sample fluid so as to prevent contamination.

One such method is the use of available ion exchange resin. Ion exchange resins are usually housed in disposable cartridges which would be a suitable option if the monitoring equipment needed to be portable.

The envisaged system could consist of an in-line ion exchange unit through which the sampled fluid would flow. The dimensions of the unit would be determined by calculation. Again, attention would only be necessary when the resin material was near to the end of its working life, which would be likely to be considerable since only low concentrations of material would be required to be extracted.

Alternatively, a method which operates in a similar way to that of the above cell could be used. A potential would be applied to an additional electrode located down stream which trap these species onto the electrode's surface. The knowledge of the potential or ranges of potentials to recover some or all of the mercury present in the solution would be necessary. However, when all the required potentials had been determined, the process could be very efficient and would only require maintenance when a given electrode surface could no longer absorb any more material. Maintenance in this situation would be likely to involve replacement of the full electrode with a new one. The application of this technique would be suitable for the dedicated instrument system. A preferred arrangement would comprise a contaminated sample flowing through a porous carbon matrix which has a suitable electrical potential applied to it causing the species in solution to be retained in the matrix.

Preferably, the housing means comprises a container coated with an inert shroud, the inert shroud comprising a semi-permeable member such as a sintered end cap. Ideally, the inert shroud is PTFE. Ideally, the sintered end cap is made from vyon. Vyon is a trade name of a hydrophobic, porous, close-pored durable plastic material.

The use of electrochemical stimulated migration of mercury species ensures that control and limited dissolution of the species takes place. This is achieved by controlling the amount of current applied. Thus mercury ions can be selectively added to a sample stream in a controlled way for the purpose of taking analytical measurements. This controlled addition of mercury ions is therefore highly desirable.

According to a second aspect of the invention there is provided a method for adding mercury ions to a fluid sample within a flow through sample system comprising:

housing a pre-determined amount of liquid mercury in a housing means, the housing means comprising a semi-permeable part which is in fluid contact with a main sample stream conduit wherein there is a first electrode which is in direct electrical contact with only the mercury;

causing a current to flow between the first electrode and a second electrode located either within the housing means or within the main sample stream whereby mercury ions produced within the housing means migrate from the housing means through the semi-permeable part into the sample fluid.

The mercury ions can be collected on an analysis electrode located downstream of the housing means, enabling a sample measurement to be made.

Indeed, using prior art techniques the mercury salts introduced into a sample stream, as mentioned above, can be later plated onto an analysis electrode surface. However, at the end of a measurement, the mercury may be required to be removed before the next measurement is made. This means that the mercury is continually plated and removed from the electrode surface during the analysis procedure. Thus, the mercury is only used for a single measurement. The spent mercury ions re-enter the sample stream. The sample stream is then ejected into the environment from which it was originally taken or is put to waste.

In contrast to the above conventional techniques where mercury salt is added to the sample solution and subsequently plated onto an electrode using a potential, the degree of contamination using the method in accordance with the invention is significantly reduced. This is, in part, because in a portable system the method and apparatus of the invention is, ideally, only used once before taking the apparatus out for use. The mercury is not stripped off but used over and over again, thereby lowering the emission of mercury species into the environment. The next day, or whenever the portable apparatus is used again, another single plating can be carried out.

Using conventional mercury salt pellets with a view to providing mercury salts for the purpose of coating an electrode involves the provision of $2 \times 10^{-5}$ to $6 \times 10^{-5}$ M concentration of mercury ions in the sample fluid. Using the apparatus and method of the present invention, the aforementioned desired concentration is provided in only a fraction of the sample fluid at approximately the time when a measurement is to be taken. For example, at a fluid flow rate of 6.5 liters per hour, in order to provide a concentration of mercury ions in the order of $1 \times 100$ parts per million, 0.1304 grams of mercury are required per hour. The generation of this quantity of mercury may be achieved using a current. Thus a current is passed through a mercury cell system end maintained by a constant current circuit during the taking of readings.

The aforementioned method of the invention is practiced using a specifically designed apparatus.

BRIEF DESCRIPTION OF THE DRAWINGS

An embodiment of the invention will now be provided by way of example only with reference to the accompanying drawing wherein.

DETAILED DISCUSSION OF PREFERRED EMBODIMENTS

Figure 1:
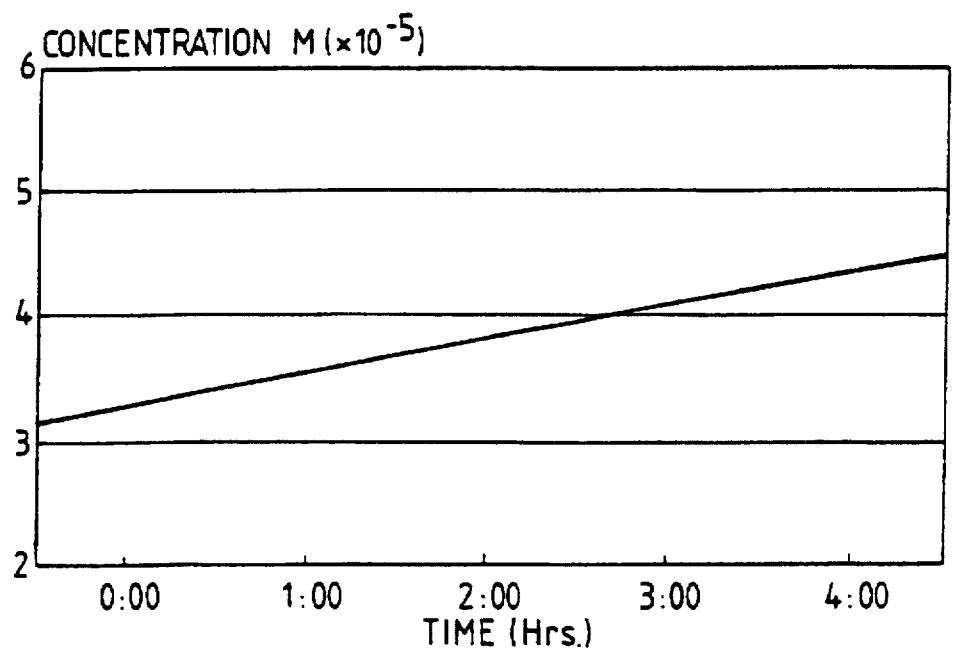
FIG. 1 represents a graph showing the dissolution rate of a pellet of a mercury salt.

Referring firstly to FIG. 1 there is shown a graph illustrating the conventional relatively uncontrolled dissolution rate of a pellet of mercury salt over time at a concentration of $10^{-5}$ M. It can be seen that concentrations of $10^{-5}$ M of mercury salt are continuously added to a sample stream over a period of approximately four hours. Depending upon the size of the sample stream, the amount of mercury added using conventional techniques can be considerable.

Figure 2:
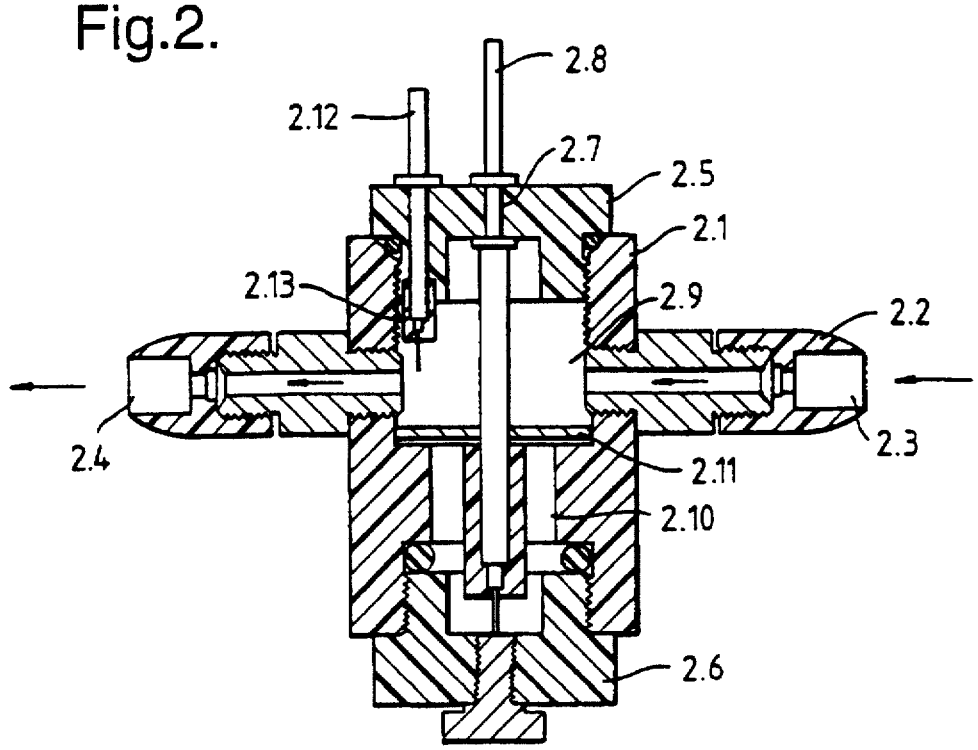
FIG. 2 represents a side sectional view of an apparatus in accordance with the invention.

FIG. 2 represents an apparatus in accordance with the present invention which significantly reduces the amount of mercury added to a sample stream. The apparatus comprises a main housing 2.1 ideally made of PTFE through which a sample stream, as indicated by arrows, flow. The sample stream is housed within a PTFE pipe fitting, 2.2, which forms the main sample stream conduit including an inlet 2.3, and an exit, 2.4.

Either end of the housing 2.1 is provided with an upper end cap 2.5 and a lower end cap 2.6, the caps being made of PTFE.

The upper end cap 2.5 is provided with a centrally positioned through bore 2.7 which is adapted to receive electrode 2.8.

Within housing 2.1 there is provided a central sample chamber 2.9 and the housing means or mercury chamber, 2.10. Chambers 2.9 and 2.10 are separated by a sintered vyon member 2.11 which is permeable to the mercury.

Electrode 2.1 penetrates bore 2.7 and extends through the central chamber 2.9 end sintered vyon member 2.11 into the mercury chamber 2.10. Within the mercury chamber 2.12, a PTFE shroud is provided to shroud the majority of the lower end of electrode, 2.8 from the chemical species housed within the mercury chamber 2.10. However, the lowermost end of the electrode 2.8 penetrates the shroud and thus makes contract with the mercury housed within the bottom of the mercury chamber 2.10.

Central chamber 2.9 further includes a second electrode 2.12 whose lowermost tip is similarly shrouded via PTFE shroud 2.13. However, the lowermost end of the electrode member penetrates beyond the shroud and is thus exposed to sample fluid flowing through sample pipe 2.2 and chamber 2.9.

In use, a potential is applied across the two electrodes 2.8 and 2.12, electrode 2.8 being located in the mercury contained in chamber 2.10 and electrode 2.12 being located in the sample stream. This has the effect of causing migration of micromolar concentrations of Hg++ and Hg2++ ions from the mercury pool through the partitioning sintered disk 2.11 into the sample stream. By applying a suitable potential the mercury ionic species is subsequently collected at an analysis electrode downstream of the mercury chamber 2.10.

A current (for example of 23 milliamps) is passed through the mercury chamber 2.10 and maintained by a constant current circuit. The system can operate for very long periods over many weeks before requiring attention by way of addition of mercury to the cell.

Verification that mercury plating is successful using an apparatus and method in accordance with the invention is obtained by showing that mercury can be deposited from solution onto an analysis electrode and removed therefrom using conventional ASV methods. Thus, once mercury has been plated onto the analysis electrode it can be removed therefrom using ASV techniques and detected downstream by electrochemical analysis.

As mentioned, the mercury cell supplies mercury ions which are deposited on the working electrode of the analysis cell downstream. To test to see of one has the right concentration of mercury ions and conditions for plating the right amount of mercury on the analysis electrode the following is carried out:

One can attempt to plate onto the analysis electrode downstream when the mercury cell is in operation. This is carried out by (a) passing current through the mercury cell for a period of time and then switch off; (b) by holding the potential of the analysis electrode at −1.3volts with respect to a AgCl, AgKCl reference electrode for a comparable period and at the same time as (a). This is carried out while a dilute solution of an electrolyte is passing through the system. After attempting plating and to determine whether there is sufficient mercury on the analysis electrode, its potential is increased to about +0.1 volts in order to strip off the mercury.

If this exercise is carried out by linear sweep techniques, involving a potentiostat, waveform generator, as well as an XY plotter, a voltammogramme may be produced. The dissolution of the previously plated mercury will be seen as a peak, on the current axis, whose magnitude is directly proportional to the thickness of the plating. Experimental procedure is simple if perhaps time consuming and involves producing voltammogrammes of controlled solutions, for example, sample fluid collected before mercury salts are added, clean sample solutions spiked with a known concentration of mercury salts and finally samples of solution collected after the addition of mercury salts at various time intervals. Samples of distiled water are also occasionally passed through the potentiostat system so as to ensure adequate cleaning at the electrode surface has been carried out. The concentration of mercury required in the solution to produce the voltammogramme is small and so is not missed by the analysis employing the potentiostat. A halt in the potential sweep is used to a potential of around −1.3 volts with respect to AgKCl, AgCl references to allow for an accumulation or deposition of mercury from dissolved mercury species by its reduction. Deposition times are normally between 10 to 120 seconds depending on conditions.

FIGS. 3A to 3D represent the affects and differences in response of the various test and sample solutions, as well as the increases in observed and measured peak height, as a result of increase in the time for deposition of mercury onto the electrode surface.

The plots are derived from a small three electrode cell, a potentiostat and a waveform generator. The cell contains a glass carbon working, platinum counter and a silver chloride, silver potassium chloride reference. The cell volume allows for about 50 cc of sample fluid. The voltage is held at around −350 millivolts for 30 seconds. This is used to increase the sensitivity of determination.

Figure 3A:
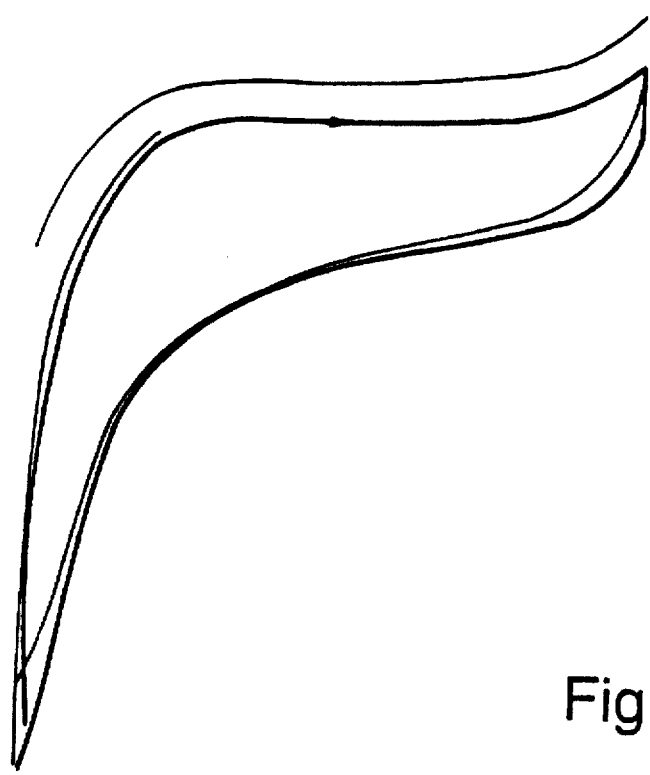
FIGS. 3A, B, C and D show CV plots derived from a small three electrode cell, a potentiostat and waveform generator.
Figure 3B:
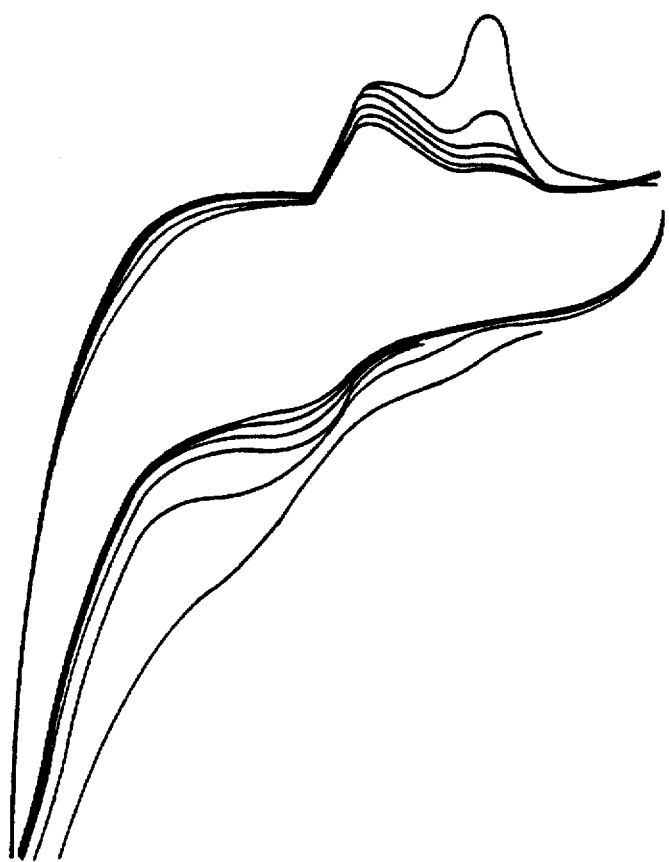
Figure 3C:
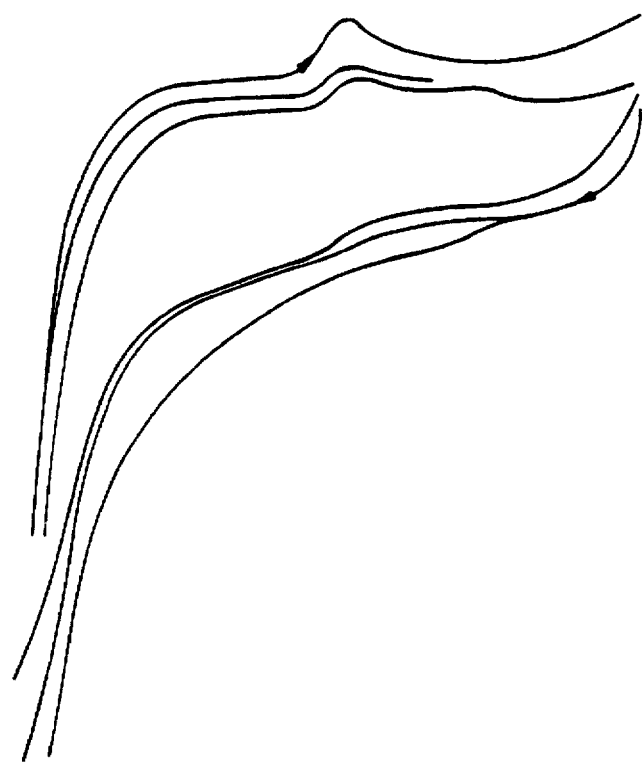
Figure 3D:
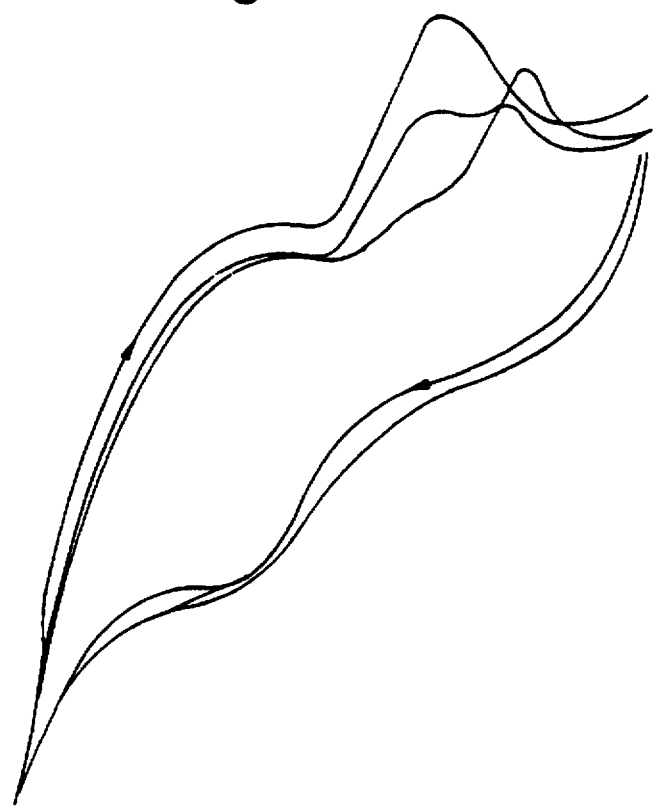

FIG. 3A shows a sweep with only distiled water containing sodium nitrate at 0.1 M concentration to increase conductivity. FIG. 3B, for calibration purposes, is shown as a sweep and successive lowering sweeps after the 30 second hold with the addition of $5 \times 10^{-5}$ M $Hg(NO_3)_2.NaNO_3$ solution. The figure shows a peak typical of the dissolution of mercury subsequent and due to deposition during 30 second hold. FIG. 3C shows the analysis of a sample of water carrying 0.1 mole of sodium nitrate being passed through the mercury cell. It is clearly seen that mercury ion species has been generated by the cell and is now being detected in the water passing through. A similar result is seen without the use of sodium nitrate as a cell to increase electrical conductivity. The absolute vale of peak is lower but is just as distinct after a 30 second hold. Clearly, the mercury cell is feasible.

I claim:

1. Apparatus for adding mercury ions to a sample fluid within a flow-through sensor system comprising housing means, at least part of which is in fluid connection with a main sample stream conduit, at least part of the housing means in fluid connection with the main sample stream conduit being semi-permeable;

a first electrode located within the housing means which is designed so that it would be in direct electrical contact only with the mercury when the mercury is located within the housing means;

and a second electrode located either within the housing means or within the main sample stream conduit;

the apparatus being arranged such that when mercury is located within the housing means and an electrical current is passed between the first and second electrodes, mercury ions are formed in the housing means which then are then able to migrate from the housing means via the semi-permeable part into the main sample stream conduit.

2. Apparatus as claimed in claim 1 wherein the second electrode is located within the main stream conduit.

3. Apparatus as claimed in claim 2 wherein the second electrode is in close proximity to the semi-permeable part of the housing means.

4. Apparatus as claimed in claim 1 wherein the housing means comprises a container coated with or made from an inert shroud, the inert shroud comprising a semi-permeable member.

5. Apparatus as claimed in claim 4 wherein the inert shroud is made from polytetrafluoroethylene.

6. Apparatus as claimed in claim 4 wherein the semi-permeable member is a sintered end cap.

7. Apparatus as claimed in claim 6 wherein the sintered end cap is made from a hydrophobic, porous, close-pored durable plastic material.

8. A method for adding mercury ions to a fluid sample within a flow through sample system comprising:

housing liquid mercury in a housing means, the housing means comprising a semi-permeable part which is in fluid contact with a main sample stream conduit wherein there is a first electrode which is in direct electrical contact with only the mercury;

causing a current to flow between the first electrode and a second electrode located either within the housing means or within the main sample stream conduit whereby the mercury ions produced within the housing means migrate from the housing means through the semi-permeable part into the sample fluid in the sample stream conduit.

* * * * *